US007715897B2

(12) United States Patent
Coulston

(10) Patent No.: US 7,715,897 B2
(45) Date of Patent: *May 11, 2010

(54) EXTENDED OPTICAL RANGE REFLECTIVE SYSTEM FOR MONITORING MOTION OF A MEMBER

(75) Inventor: George W. Coulston, Pittsburgh, PA (US)

(73) Assignee: Textronics, Inc., Wilmington, DE (US)

( * ) Notice: Subject to any disclaimer, the term of this patent is extended or adjusted under 35 U.S.C. 154(b) by 519 days.

This patent is subject to a terminal disclaimer.

(21) Appl. No.: 10/937,119

(22) Filed: Sep. 9, 2004

(65) Prior Publication Data

US 2005/0106977 A1    May 19, 2005

Related U.S. Application Data

(60) Provisional application No. 60/502,760, filed on Sep. 12, 2003, provisional application No. 60/502,751, filed on Sep. 12, 2003, provisional application No. 60/502,750, filed on Sep. 12, 2003, provisional application No. 60/526,187, filed on Dec. 2, 2003, provisional application No. 60/526,429, filed on Dec. 2, 2003, provisional application No. 60/526,188, filed on Dec. 2, 2003.

(51) Int. Cl.
*A61B 5/02* (2006.01)

(52) U.S. Cl. ............. 600/407; 250/559.4; 250/559.01; 250/559.12; 250/559.16; 250/222.1; 250/221; 356/238.1; 356/238.2; 356/238.3; 356/239.1; 356/239.2; 356/239.3; 356/429; 356/430; 356/431; 2/1; 442/182; 442/184; 442/301; 600/473; 600/476; 600/479; 600/534; 600/595

(58) Field of Classification Search ............... 442/182, 442/184, 301, 306; 600/485, 490, 499, 407, 600/473, 476, 479, 534, 595; 2/1; 250/221, 250/559.4, 559.01, 559.12, 559.16, 222.1; 356/238.1–239.3, 429–431
See application file for complete search history.

(56) References Cited

U.S. PATENT DOCUMENTS 4,909,260 A    3/1990    Salem et al.

(Continued)

FOREIGN PATENT DOCUMENTS

WO    97/14357    4/1997

OTHER PUBLICATIONS

Salutron Technology Evaluation Data Summary from www.Salutron.com, Apr. 26, 2005.

*Primary Examiner*—Elizabeth M Cole
(74) *Attorney, Agent, or Firm*—Connolly Bove Lodge & Hutz LLP

(57) ABSTRACT

A garment and system includes a monitoring fabric that exhibits a light reflection property and substantially no light transmission property when the fabric is illuminated with light having wavelength(s) in the range of 400 to 2200 nanometers. The amount of useful light reflected by the fabric into an aperture of acceptance defined with respect to an axis extending from the fabric relative to the amount of light lost to the aperture of acceptance detectably changes when the fabric stretches in response to motion, as the motion induced by physiological activity (e.g., heart rate). The system includes at least one radiation source and at least one radiation detector, with the detector disposed in the aperture of acceptance. The source and detector may be attached to the fabric in relative positions such that the reception of incident radiation by the detector is directly affected by a change in the amount of useful light reflected by the fabric into the aperture of acceptance as the fabric stretches in response to motion.

10 Claims, 5 Drawing Sheets

U.S. PATENT DOCUMENTS

| | | |
|---|---|---|
| 4,920,969 A | 5/1990 | Suzuki et al. |
| 5,577,510 A | 11/1996 | Chittum et al. |
| 5,703,688 A | 12/1997 | Bell |
| 5,840,037 A | 11/1998 | Tochikubo et al. |
| 6,168,567 B1 | 1/2001 | Pickering et al. |
| 6,224,558 B1 | 5/2001 | Clemmons |
| 6,315,009 B1 | 11/2001 | Jayaraman et al. |
| 6,322,516 B1 | 11/2001 | Masuda et al. |
| 6,341,504 B1 | 1/2002 | Istook |
| 6,360,615 B1 | 3/2002 | Smela |
| 6,842,722 B2 | 1/2005 | David |
| 2003/0095263 A1 | 5/2003 | Varshneya et al. |
| 2005/0118914 A1 | 6/2005 | Kuo et al. |
| 2005/0277837 A1 | 12/2005 | Coulston et al. |
| 2007/0042179 A1 | 2/2007 | Karayianni et al. |

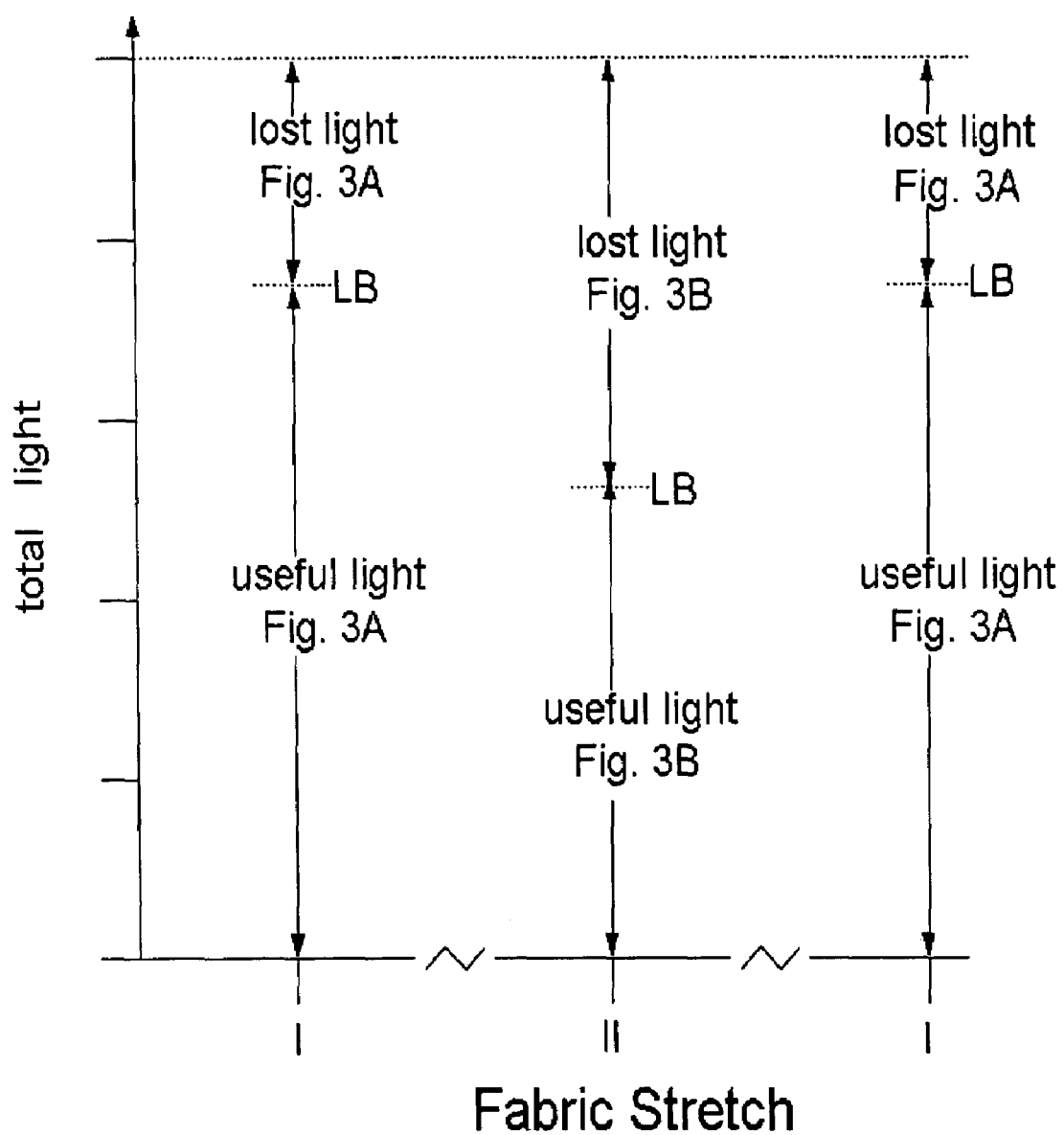

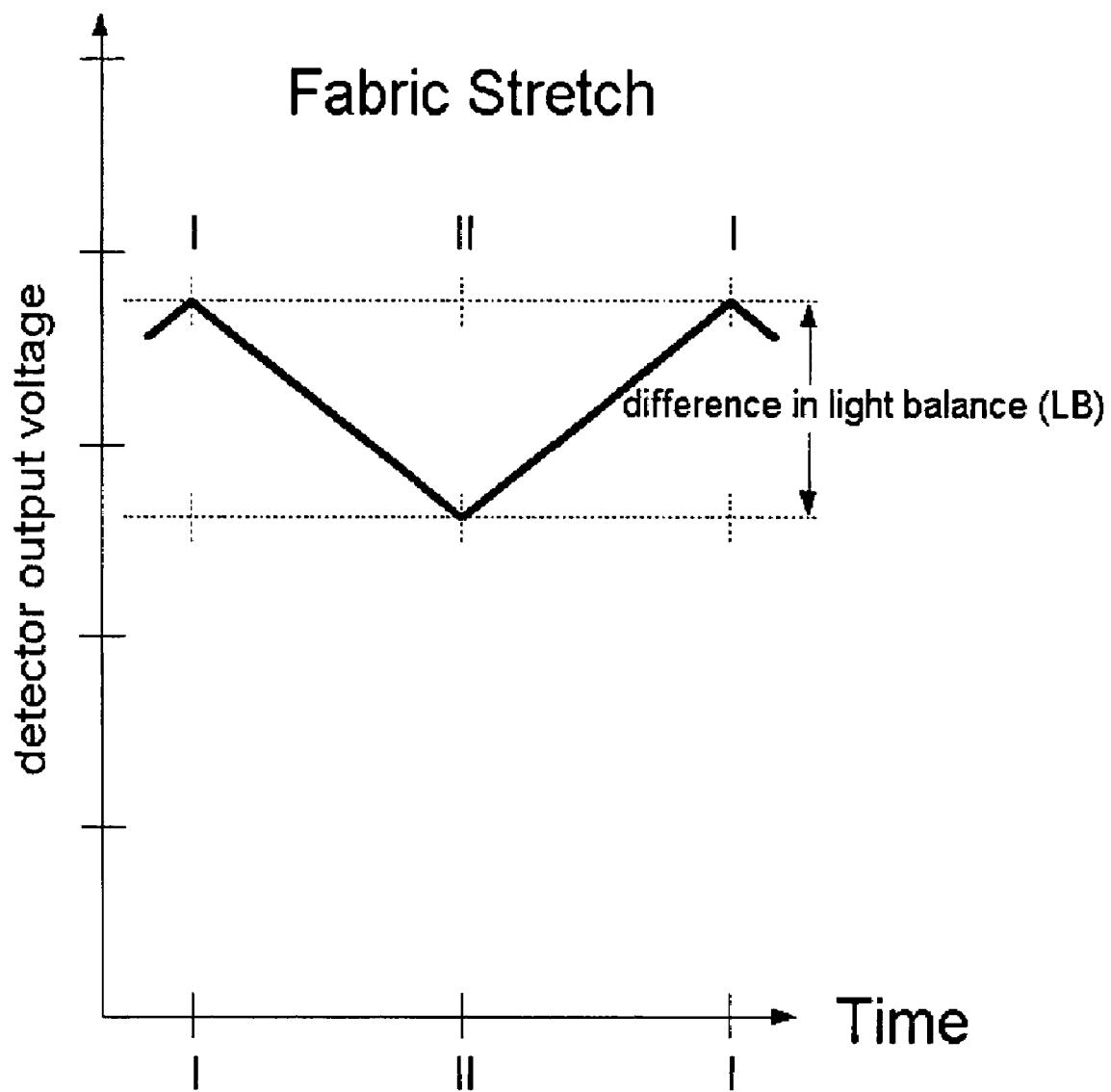

EXTENDED OPTICAL RANGE REFLECTIVE SYSTEM FOR MONITORING MOTION OF A MEMBER

CROSS-REFERENCE TO RELATED APPLICATIONS

Subject matter disclosed herein is related to the following co-pending applications:

System for Monitoring Motion of a Member, U.S. application Ser. No. 60/502,760; filed Sep. 12, 2003 in the name of Chia Kuo and George W. Coulston.

Blood Pressure Monitoring System and Method, U.S. application Ser. No. 60/502,751; filed Sep. 12, 2003 in the names of George W. Coulston and Thomas A. Micka.

Reflective System for Monitoring Motion of a Member, U.S. application Ser. No. 60/502,750; filed Sep. 12, 2003 in the name of George W. Coulston;

Blood Pressure Monitoring System and Method Having Extended Optical Range, U.S. application Ser. No. 60/526,187; filed Dec. 2, 2003 in the names of George W. Coulston and Thomas A. Micka.

Extended Optical Range Reflective System for Monitoring Motion of a Member, U.S. application Ser. No. 60/526,429; filed Dec. 2, 2003 in the name of George W. Coulston.

Extended Optical Range System for Monitoring Motion of a Member, U.S. application Ser. No. 60/526,188; filed Dec. 2, 2003 in the name of Chia Kuo and George W. Coulston.

BACKGROUND OF THE INVENTION

1. Field of the Invention

This invention relates to a fabric useful in a system for monitoring motion, and to the monitoring system incorporating such fabric. One such type of motion that can be monitored is that associated with geometric change in a body in response to physiological activity.

2. Description of the Prior Art

Heart rate monitors are known for measuring and reporting the heart beat of humans and animals. Such monitors receive signals from the pulsating flow of blood synchronized with the periodic pumping activity of the heart. Typically, these well-known monitors detect the pulsating flow of blood through a sensor in a chest belt or through a sensor clipped mechanically to an ear or finger. U.S. Pat. No. 5,820,567 (Mackie) describes a representative arrangement of a chest belt or an ear clip for a heart rate sensing apparatus.

A chest belt is difficult to fit and often requires gel to wet the sensor electrodes prior to use. Tight chest belts for heart monitoring can be uncomfortable if worn for a prolonged period. Mechanical sensors that clip to a finger or an ear can also be uncomfortable.

The QuickTouch™ heart monitor sold by Salutron Inc. (Fremont, Calif. 94538, USA) eliminates the chest strap, finger or ear clip to measure heart rate in all phases of exercise. However, while eliminating cumbersome wires and straps, two points of body contact are required in operation. This device thus requires application of two fingers on a watch band, two hands on a treadmill, or two hands on a bicycle handle bar to give heart rate readings. As a result this device does not totally free the subject from the monitoring process.

Systems that relieve the monitored subject from the discomfort of chest belts or clip devices to the finger or ear, and from the inconvenience of being restricted to the monitoring apparatus, have been disclosed.

U.S. Pat. No. 6,360,615 (Smela) discloses a monitoring system using a garment that detects motion in the body of the wearer through a strain gauge implemented using a polypyrrole-treated fabric.

U.S. Pat. No. 6,341,504 (Istook) discloses a garment for physiological monitoring comprising one or more elongated bands of elastic material with conductive wire formed in a curved pattern. When the garment is worn by a human, the elongation and relaxation of the fabric caused by geometrical changes of the human frame induce electrical property changes in the conductive wire(s) of the garment. Such a system adds an additional component of complexity to the fabric structure, which is not well-suited to traditional garment design and construction.

U.S. Pat. No. 4,909,260 (Salem) describes a bulky waist belt system for physiological monitoring.

U.S. Pat. No. 5,577,510 (Chittum) describes bulky chest and waist belts for physiological monitoring.

Patent Publication WO 9714357, Healthcare Technology Limited, Great Britain discloses a monitor capable of generating an audio heartbeat message.

SUMMARY OF THE INVENTION

The present invention is directed to a fabric, garment, system, and method for monitoring motion of a member, and is believed particularly useful for the monitoring of the motion generated by geometric changes in the body of a subject in response to physiological activity. By monitoring such motion, a noninvasive measurement of a parameter characterizing the physiological activity may be derived.

The fabric exhibits a light reflection property and substantially no light transmission property when the fabric is illuminated with light having a wavelength in the range of from about 400 nanometers to about 2200 nanometers, and particularly in the ranges from about 400 to about 800 nanometers and from about 700 to about 2200 nanometers.

The amount of useful light reflected by the fabric into an aperture of acceptance, defined with respect to an axis extending from the fabric relative to the amount of light lost to the aperture of acceptance, changes when the fabric stretches and recovers in response to motion. Such motion could be induced, for example, by geometric changes in the body caused by physiological activity.

In the preferred instance the fabric is comprised of a plurality of reflective yarns each having a coating of an electrically conductive material thereon knitted or woven with a second plurality of stretchable yarns. Each stretchable yarn is formed as a combination of a covered elastic yarn and a hard yarn.

The fabric may be used as a monitoring patch in a variety of settings including a garment or textile mantle.

The garment or textile mantle having the patch of monitoring fabric disposed thereon or therein may be incorporated into a system for monitoring motion, such as the motion generated by geometric changes in the body of a subject due to physiological activity. The system further includes a source providing radiation with wavelength(s) in the range of from about 400 nanometers to about 2200 nanometers, and particularly in the ranges from about 400 to about 800 nanometers and from about 700 to about 2200 nanometers. The system still further includes at least a detector responsive to incident radiation in the same wavelength range and sub-ranges.

The detector is located in an aperture of acceptance defined about an axis extending from the fabric. The source and detector preferably are attached to the fabric in relative positions such that the reception of incident radiation by the detector is directly affected by a change in the amount of useful light reflected by the fabric into the aperture of acceptance as the fabric stretches. Such changes occur when the fabric stretches in response to motion due to geometric changes in the body of a subject S wearing the garment or in the body component having the mantle thereon. A signal processor converts a signal from the detector representative of radiation incident thereon into a signal representative of at least one predetermined physiological parameter of the subject wearing the garment.

Alternatively, the system can comprise more than a single radiation source and more than a single radiation detector for each source. In such an alternative embodiment, the signal processor is responsive to signals from more than a single radiation source and more than a single radiation detector and converts these signals into a signal representative of one or more predetermined physiological parameters associated with the subject wearing the garment.

BRIEF DESCRIPTION OF THE DRAWINGS

The invention will be more fully understood from the following detailed description, taken in connection with the accompanying drawings, which form a part of this application, and in which:

FIG. 3C is a graphical representation of the change in the light balance, that is, the amount of useful light reflected by the fabric into an aperture of acceptance relative to the amount of light lost to the aperture of acceptance as the fabric stretches and recovers;

FIG. 3D is a graphical representation of a signal, periodic in time, representing the change in the light balance during stretching and recovery of the fabric.

DETAILED DESCRIPTION OF THE INVENTION

Figure 1:
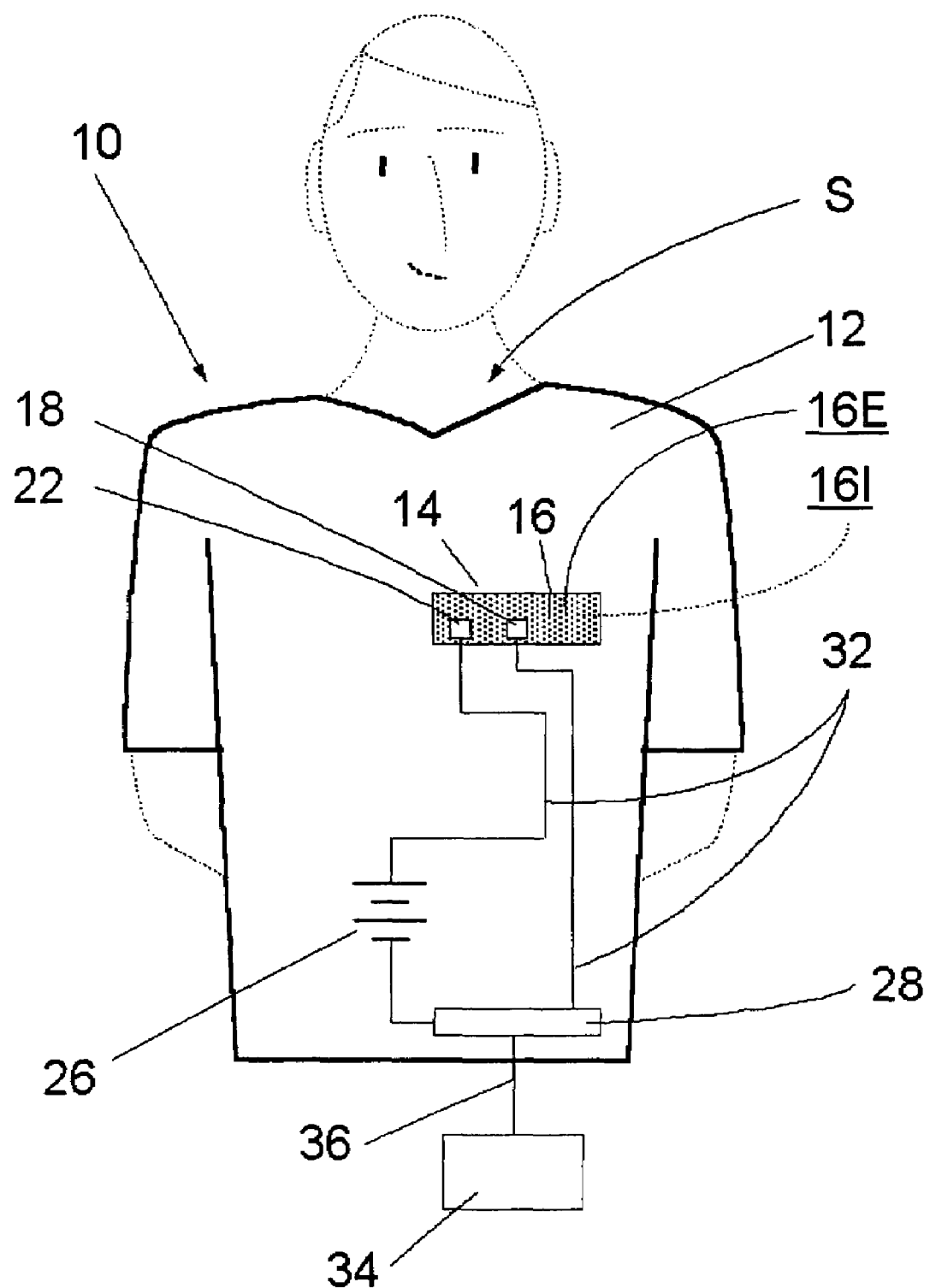
FIG. 1 is a stylized pictorial representation of a system for monitoring at least one physiological parameter of a subject S that includes a garment having a fabric in accordance with the present invention included therein, where the garment is sized to be worn over the torso of the subject S.

Throughout the following detailed description similar reference characters refer to similar elements in all figures of the drawings.

FIG. 1 is a stylized pictorial representation of a motion monitoring system 10 in accord with the present invention as applied to the task of monitoring motion due to geometric changes of the body of a subject S in response to physiological activity. A noninvasive measurement of one or more parameter(s) characterizing the physiological activity of the subject S, such as heart or breathing rate, may be derived by monitoring such motion(s).

As seen in FIG. 1, the system 10 includes a garment 12 having at least a portion, or patch 14, formed from a monitoring fabric 16. The monitoring fabric 16 has an exterior or outer surface 16E presented to a viewer and an interior surface 16I presented to the body of the subject S. The patch 14 of the monitoring fabric 16, although shown as rectangular in FIG. 1, may take any convenient shape. For example, the patch may be circular, oval in shape, or may be any regular or irregular shape. If desired, a portion or even the entirety of the garment 12 may be made from the monitoring fabric 16.

The monitoring fabric 16 in accordance with the present invention exhibits a light reflection property and substantially no light transmission property when the fabric is illuminated with light having a wavelength in the extended range from about 400 to about 2200 nanometers. This range is extended in the sense that it encompasses both near infrared light and visible broad spectrum white light having wavelengths in the visible spectrum.

As used herein the term "broad spectrum white light" means light having a wavelength in the range from about four hundred (400) nanometers to about eight hundred (800) nanometers.

As used herein the term "near infrared light" means light having a wavelength in the range from about seven hundred (700) nanometers to about two thousand two hundred (2200) nanometers. The wavelength of 805 nanometers or the wavelength of 880 nanometers may be used for systems operating in the near infrared spectrum. Light having wavelength of 805 nanometers is preferred.

Figure 2:
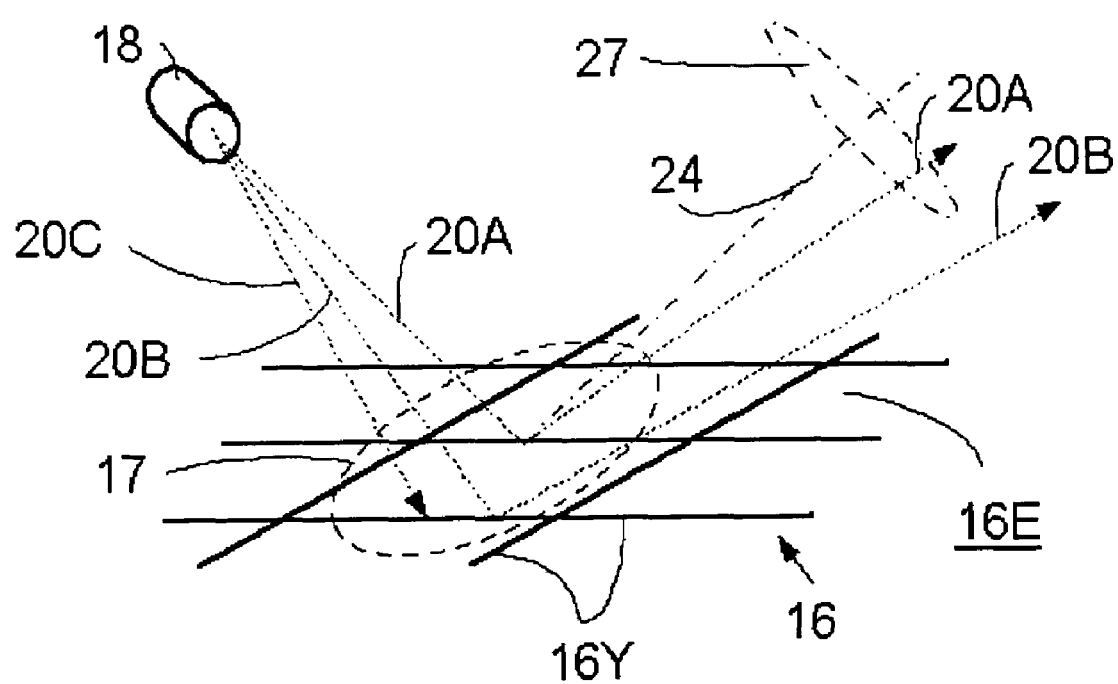
FIG. 2 is a stylized representation illustrating the reflective response of the fabric of the present invention.

FIG. 2 shows by way of a stylized diagrammatic illustration the reflective response of the fabric 16 in accordance with the invention. The amount of useful light reflected by the fabric 16 through an aperture of acceptance 27 changes as the fabric stretches and recovers. The aperture of acceptance 27 is shown by way of illustration in FIG. 2 as an area of any predetermined shape (e.g., circular in FIG. 2) spaced a predetermined distance from the surface of the fabric 16 and centered upon a predetermined reference axis 24 extending from the surface of the fabric 16.

The term "light balance" may be used throughout this application to refer to the amount of useful light reflected by the fabric relative to the amount of light lost. The term "useful light" refers to that amount of light originally incident upon an illuminated region 17 of the fabric that is reflected from the fabric 16 through an aperture of acceptance 27 defined with respect to a reference axis 24 extending from the fabric 16. "Lost light" refers to light originally incident upon an illuminated region 17 that is not reflected into the aperture of acceptance 27.

Light could be "lost" to the aperture of acceptance 27 for various reasons. For example, movement of the fabric 16 causes light reflected from the fabric 16 to diverge with respect to the axis 24 and miss the aperture of acceptance 27. Otherwise, incident light could become "lost" when absorbed into the material of which the fabric 16 is formed.

The monitoring fabric 16 used in the patch 14 can be made from a reflective yarns, stretchable yarns any combination of reflective and stretchable yarn or any like material. In one exemplary construction a first plurality of reflective yarns is combined with a second plurality of stretchable yarns.

The yarns can be combined in any conventional manner including woven or non-woven construction. For woven constructions, yarns can be combined in plain weave, satin weave, twill weave or any other well known constructions. For non-woven constructions such as knit constructions, yarns can be combined by circular knit, warp knit or any other suitable knit construction. In circular knits, typical constructions are single jersey (i.e. different structure in front and back) and double jersey (i.e. same structure in front and back). Warp knits may include tricot and raschel constructions where the tightness can be adjusted by adjusting the number of needles/inch or the stitch size.

Any suitable apparel denier and any suitable needle combination or warp/weft intensity may be used in making the monitoring fabric. Each reflective yarn may comprise a coating of a specularly reflective material thereon. The coating may also be electrically conductive. Furthermore, the reflective yarn may be elastic. Each stretchable yarn is formed as a combination of an elastic yarn component and a hard yarn component.

In the preferred instance the reflective yarn is that yarn sold by Laird Sauquoit Technologies, Inc. (300 Palm Street, Scranton, Pa., 18505) under the trademark X-static® yarn. X-static® yarn is based upon a 70 denier (77 dtex), 34 filament textured nylon available from INVISTA North America S. à r. I., Wilmington, Del. 19805, as product ID 70-XS-34X2 TEX 5Z that is electroplated with electrically-conductive silver.

Alternatively, another method of forming the monitoring fabric 16 is to screen-print a pattern using an electrically conductive ink after constructing the yarns in any conventional woven or non-woven manner. Suitable electrically conductive inks include, but are not limited to, those sold by DuPont Microcircuit Materials, Research Triangle Park, N.C. 27709, as silver ink 5021 or silver ink 5096, and the like.

A screen-printed pattern of conductive inks must also allow the fabric to move. Preferably, the conductive ink does not affect the ability of the fabric to stretch and recover. One way to prevent affecting the stretch and recovery properties of fabric is to screen-print a pattern of conductive ink(s) in the form of a matrix of dots. Such a dot matrix pattern provides full freedom for the yarns in the fabric to move, while still exhibiting desired light reflection and non-transmission properties.

The patch 14 of monitoring fabric 16 can alternatively be formed from elastic and electrically conductive composite yarn comprising a core yarn made of, for instance, LYCRA® spandex yarn wrapped with insulated silver-copper metal wire obtained from ELEKTRO-FEINDRAHT AG, Escholzmatt, Switzerland, using a standard spandex covering process. The core yarn may further be covered with any nylon hard yarn or polyester hard yarn.

Stretchable yarn can be formed in any conventional manner. For example, the stretchable yarn can be formed as a combination of a covered elastic yarn and a hard yarn.

In one preferred embodiment, the covered elastic yarn can be comprised of a twenty (20) denier (22 dtex) LYCRA® spandex yarn single-covered with a ten (10) denier (11 dtex) seven filament nylon yarn. LYCRA® spandex yarn is available from INVISTA North America S. à r. I., Wilmington, Del. 19805. Alternatively, the elastic yarn component of the present invention may comprise elastane yarn or polyester bicomponent yarns such as those known as ELASTERELL-P™ from INVISTA S. à r. I. North America Inc. of Wilmington, Del. The terms spandex and elastane are used interchangeably in the art. An example of a branded spandex yarn suitable for use with the present invention is LYCRA®.

Synthetic bicomponent multifilament textile yarns may also be used to form the elastic yarn component. One preferred synthetic bicomponent filament component polymer can be thermoplastic. The synthetic bicomponent filaments can be melt spun or formed in any other manner common in the art of filament formation. In the most preferred embodiment the component polymers can be polyamides or polyesters.

A preferred class of polyamide bicomponent multifilament textile yarns comprises those nylon bicomponent yarns which are self-crimping, also called "self-texturing". These bicomponent yarns comprise a component of nylon 66 polymer or copolyamide having a first relative viscosity and a component of nylon 66 polymer or copolyamide having a second relative viscosity, wherein both components of polymer or copolyamide are in a side-by-side relationship as viewed in the cross section of the individual filament. Self-crimping nylon yarn such as that yarn sold by INVISTA North America S. à r. I., Wilmington, Del. 19805 under the trademark TACTEL® T-800™ is an especially useful bicomponent elastic yarn.

Some examples of polyester component polymers include polyethylene terephthalate (PET), polytrimethylene terephthalate (PTT) and polytetrabutylene terephthalate. In one preferred embodiment polyester bicomponent filaments comprise a component of PET polymer and a component of PTT polymer in a side-by-side relationship as viewed in the cross section of the individual filament. One exemplary yarn having this structure is sold by INVISTA North America S. à r. I., Wilmington, Del. 19805 under the trademark T-40™ Next Generation Fiber.

The hard component could be made from any inelastic synthetic polymer fiber(s) or from natural textile fibers, such as wool, cotton, ramie, linen, rayon, silk, and the like. The synthetic polymer fibers may be continuous filament or staple yarns selected from multifilament flat yarns, partially oriented yarns, textured yarns, bicomponent yarns selected from nylon, polyester or filament yarn blends. The hard component is preferably 260 denier (286 dtex) 68 filament nylon yarn.

Nylon yarns may comprise synthetic polyamide component polymers such as nylon 6, nylon 66, nylon 46, nylon 7, nylon 9, nylon 10, nylon 11, nylon 610, nylon 612, nylon 12 and mixtures and copolyamides thereof are preferred. In the case of copolyamides, especially preferred are those including nylon 66 with up to 40 mole percent of a polyadipamide wherein the aliphatic diamine component is selected from the group of diamines available from E. I. Du Pont de Nemours and Company, Inc. (Wilmington, Del. USA, 19880) under the respective trademarks DYTEK A® and DYTEK EP®. Further in accordance with the present invention, the hard yarn portion of the present invention may comprise polyesters such as, for example, polyethylene terephthalate, polytrimethylene terephthalate, polybutylene terephthalate and copolyesters thereof.

The monitoring fabric 16 used in the patch 14 can be made according to any conventional textile means, including warp knitting, weft knitting, weaving, braiding, or through nonwoven construction. The yarns can be combined to achieve fabrics exhibiting varying elasticity, including but not limited to weft elastic, warp elastic or bielastic fabrics.

The monitoring fabric 16 may also be formed from composite yarns in which the reflective and stretchable components are combined in the same yarn. Such a composite yarn would include a covering yarn having a spectrally reflective outer surface that is wrapped about an elastic yarn component in one or more layers.

The remainder of the structure of the garment 12 may exhibit any convenient textile construction (e.g., knitting, weaving) and may be made from any suitable textile filament apparel denier yarn.

In one embodiment, the monitoring fabric 16 used in the patch 14 is attached to the garment 12. The patch 14 could be sewn, glued, taped, buttoned, interwoven or attached to the garment by any conventional means.

It alternatively lies within the contemplation of the invention that the garment 12 may be formed entirely from the monitoring fabric 16. Any suitable needle combination or warp/weft intensity may be used for the garment 12.

In another embodiment, the garment is seamlessly constructed of the monitoring fabric 16 using any suitable needle combination into the material of the remainder of the garment 12. In this context the term "seamless" refers to the known process of circular knitting on a seamless knitting machine (e.g., from Santoni S.p.A., Brescia, Italy). Garments processed in this way may possess minor seams, for example, the shoulder portion of a vest or the crotch seam of panty hose may be formed using traditionally practiced seaming methods. For these reasons the "seamless" term of art includes garments with one, or only a few seams, and substantially constructed from a single piece of fabric.

One manner in which the fabric 16 can be made to exhibit the desired reflective response with substantially no light transmission when the fabric is illuminated with light is to form the fabric in a densely woven or tightly knitted fashion. Such a densely woven fabric may be obtained by weaving yarns of, for example, ten (10) to three hundred (300) denier (11 to 330 dtex) at a density of twenty (20) to sixty (60) warp and weft yarns per centimeter. A densely knitted fabric also may be obtained by increasing the needle count in the cylinder of a circular knitting machine, or gage of the fabric, while keeping the denier of the yarn constant.

Additionally, or alternatively, fabric density may be increased by a post-weaving or post-knitting shrinking or calendering step. For example, in order to obtain a densely woven or knitted reflective fabric of the invention, a widthwise and/or lengthwise shrinking of the fabric may be obtained after wetting and re-drying on exposure to elevated temperature, about sixty (60) degrees Celsius and higher. Calendering may be performed by passing the woven or knit fabric through a nip formed between a pair of calender rolls to reduce fabric thickness and densify the fabric.

Other well known means of increasing fabric density and tightening weave patterns can be used to decrease or eliminate light transmission. For example, woven constructions can be tightened by increasing the warp ends per cm and weft ends per cm in the construction. For non-woven constructions such as knit constructions, adjusting the number of needles/inch or the stitch size can decrease or eliminate light transmission through the fabric.

The system 10 shown in FIG. 1 is adapted for monitoring the motion generated by geometric changes of the body accompanying the physiological activities of respiration or heart beat of the subject S. The garment 12 is thus configured similar to a vest or shirt, although other garment configurations are contemplated. For a vest-like or shirt-like textile structure, a contour and appropriate openings are formed for disposition on the torso of the subject S. For such use, the patch 14 of monitoring fabric 16 should be located in a position of maximum sensitivity to geometric changes in the body of the subject S. For instance, the patch 14 could be used to monitor the beating heart or the chest wall movement incident with respiration by disposing the patch 14 beneath the nipple of the left breast of the subject S. It should be understood that the physical form of the garment may be appropriately modified for disposition over other parts of the body of the subject S in the event it is desired to monitor the motion of another portion of the body which is associated with another physiological parameter.

The light balance is monitored as the monitoring fabric 16 stretches and recovers. For this purpose, the system 10 further includes a suitable source 18 of radiation operable in the wavelength range from about 400 nanometers to about 2200 nanometers, and particularly in the wavelength ranges from about 400 to about 800 nanometers and from about 700 to about 2200 nanometers. An associated detector 22 is located with respect to the fabric 16 along the reference axis 24 in the aperture of acceptance 27. The detector 22 is responsive to incident radiation in the given wavelength range and subranges for producing signals in response thereto.

The source 18 is arranged in such a way as to maintain its relative position to the detector 22. For instance, the source and detector may be rigidly connected together on one side of the fabric to maintain a spatial relationship. Alternatively, the source 18 and the detector 22 can be maintained in any conventional manner determined by the user that allows the detector to receive the radiation reflected from the monitoring fabric. Other well known means of maintaining the spatial relationship of the source relative to the detector are contemplated.

In the case of operation with near infrared light, the radiation source 18 can be a compound semiconductor-based (e.g., gallium arsenide or gallium aluminum arsenide) photo-emitting diode operating in the infrared range (at a wavelength of 805 nanometers or 880 nanometers) or any similar radiation source. The radiation detector 22 can be any device that can detect radiation, for instance, a photodiode coupled to appropriately configured output amplification stages. Any well known semiconductors can be used for forming the photodiode, including silicon or germanium. A commercially available radiation source and detector package suitable for use in the system of the present invention is that available from Fourier Systems Ltd. (9635 Huntcliff Trace, Atlanta, Ga., 30350) as model DT155 (0-5 volt output).

For broad spectrum white light (400 to 800 nanometers) operation, the source 18 can be a compound semiconductor-based "white LED" (e.g., a light emitting diode employing an indium gallium nitride based device with suitable phosphors to provide broad spectrum white light emission). The detector 22 is preferably a silicon phototransistor coupled to appropriately configured output amplification stages.

The radiation source 18 and the detector 22 are attached to monitoring fabric 16 in predetermined relative positions. The positions can be predetermined such that the reception of incident radiation by the detector 22 is directly affected by a change in the amount of light reflected by the monitoring fabric 16 into the aperture of acceptance 27 when the fabric stretches and recovers. In the preferred case, the radiation source 18 and detector 22 are embedded, or fixed firmly, into the textile structure of the monitoring fabric 16. The radiation source 18 and detector 22 can be fixed using any well known attachment method, including but not limited to, clamping, gluing, sewing, taping, or hook and loop fasteners (Velcro). Optionally, it may be desirable in some operational configurations of the invention (e.g., when the subject S is on a treadmill) to dispose both the source and the detector remote from and not in direct contact with the fabric 16. In such a remote arrangement, the radiation source 18 and detector 22 could be located in any arrangement that permits the detector 22 to detect changes in the reflection of radiation during stretch and recovery.

In the operational configuration shown in FIG. 1 (and discussed more fully in connection with FIGS. 3A and 3B) both the source 18 and the detector 22 are mounted to the exterior surface 16E of the patch 14 of monitoring fabric 16. A suitable electrical source 26 for the radiation source 18 may be conveniently carried in the garment 12. The electrical source 26 can be any conventional electrical source known in the art including, but not limited to, a battery.

The system 10 may further comprise a signal acquisition and storage unit 28 coupled to the detector 22 for storing signals produced thereby in response to incident radiation. Electrically conductive paths 32 are provided in the garment 12 to interconnect the infrared source 18, the detector 22, the electrical source 26 and the signal storage unit 28 in any appropriate electrical configuration.

One convenient manner of forming the conductive paths 32 is to knit or weave conductive filaments into the garment 12. A suitable conductive filament for such use is the X-static® yarn mentioned earlier. Alternatively, the wires could be arranged so as to be unattached to the fabric.

Another method of forming the conductive paths 32 is to screen-print the pattern of conductive paths using an electrically conductive ink. Any conductive ink could be used including, for instance, electrically conductive inks sold by DuPont Microcircuit Materials, Research Triangle Park, N.C. 27709, as silver ink 5021 or silver ink 5096. Silver ink 5021 ink is useful in fabricating low voltage circuitry on flexible substrates, while silver ink 5096 is suggested for use in situations where extreme crease conditions are encountered. While silver ink 5021 has a higher conductivity, silver ink 5096 is more easily spread and more easily builds bridges among the fibers of the fabric of the garment 12.

Once the signal is received by the radiation detector 22, a signal processor 34 may be used to convert the periodically varying signal output from the detector 22 representative of incident radiation thereon into a signal representative of at least one (or a plurality) of predetermined parameter(s) (e.g., respiration rate, heart rate) of the subject S wearing the garment 12. In the preferred instance the signal processor 34 comprises a suitably programmed digital computer. However, any signal processor known to those skilled in the art could be used.

The signals from the detector 22 stored within the storage unit 28 may be transferred to the signal processor 34 in any convenient manner for conversion into signals representative of the physiological parameter(s) of the subject S. For example, transfer between the storage unit 28 and the processor 34 may be effected by either a hardwired connection or a through-space wireless (e.g., a wireless LAN using 2.4 GHz and 802.11a/b or 802.11g protocol known to skilled practitioners of the wireless high speed data communications) or an optical transmission link, as suggested in the area indicated by reference character 36 in FIG. 1.

The signal from detector 22 is a raw signal and comprises a composite of frequencies containing at least the respiration cycle and heart rate of the subject S. Certain noise sources contribute to the overall waveform. Such noise sources are believed to arise from extraneous motion of the subject S or the monitoring fabric 16 and are not associated with respiration and heart rate. These sources of noise could be filtered using appropriate electronic filtering techniques. Specifically, high frequency and low frequency pass filters appropriately chosen can create a cleaner raw overall waveform. Such filters could be selected according to methods known to those skilled in the art in order to obtain a signal associated only with respiration or one associated only with heartbeat. Equivalently, filters to reduce known sources of signal noise are also easily employed in the data acquisition system.

Although the signal processor 34 is illustrated in FIG. 1 is disposed at a location remote from the garment, it should be understood that it lies within the contemplation of the invention to implement the processor in a suitably sized package able to be physically mounted on the garment. In such an instance the output from the detector 22 may be directly buffered into appropriate memory within the processor 34.

The operation of the motion monitoring system of the present invention may be more clearly understood with reference to FIGS. 3A through 3D. As noted earlier, both the source 18 and the detector 22 are mounted on or adjacent to the same surface of the monitoring fabric 16, typically the exterior surface 16E.

Figure 3A:
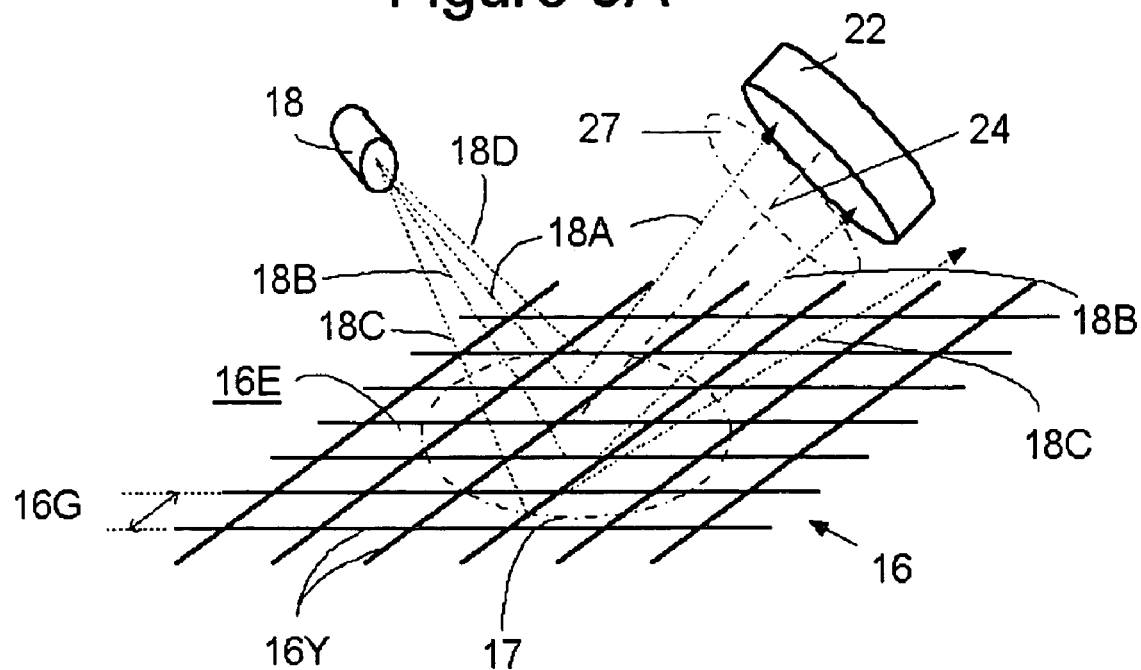
FIGS. 3A and 3B are diagrammatic views illustrating the operation of the monitoring system of the present invention.
Figure 3B:
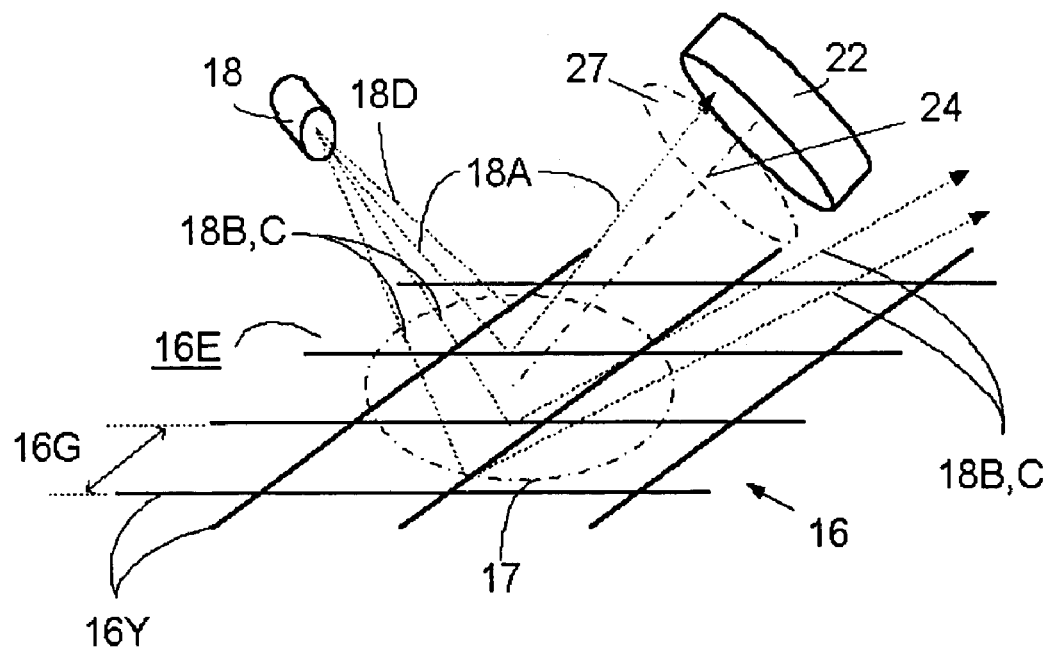

In the example illustrated in FIGS. 3A and 3B, the source 18 is positioned to illuminate a generally circular spot indicated by the reference character 17. Using appropriate optics (e.g., an objective lens on the source 18), the size of the spot 17 may be adjustably selectable to focus on an area containing any arbitrary number of yarns 16Y forming the fabric 16 or even to focus on an area containing only a single filament of a yarn 16Y.

The source 18 is arranged in such a way as to maintain its relative position to the detector 22. For instance, the source 18 and detector 22 may be rigidly connected together to maintain a spatial relationship. The radiation source 18 and detector 22 can be attached to the monitoring fabric 16 using a "clothespin" or alligator style clamp. Any well known means of maintaining the spatial relationship of the source 18 relative to the detector 22 could be used so that the photo-responsive face of the radiation detector 22 lies in and is coincident with the aperture of acceptance 27 defined with respect to the reference axis 24 extending from the fabric 16.

The monitoring operation and system are discussed in the context of monitoring the periodic physiological activity of respiration. FIG. 3A illustrates the fabric 16 in an unstretched state, while FIG. 3B illustrates the fabric 16 in a stretched state. The stretching illustrated in FIG. 3B can be caused by movements such as the periodic physiological activity of respiration. It should be noted that FIGS. 3A and 3B are schematic and are not drawn to scale. For instance, though only two dimensional movement of the fabric is shown, movement in all directions is contemplated. As discussed above, any extraneous motions of the subject S or monitoring fabric 16 could be filtered as noise using appropriate electronic filtering techniques.

As represented in FIG. 3A, in the unstretched state the filaments forming the yarns 16Y of the monitoring fabric 16 lie within a relatively close distance of each other to define a pattern of relatively narrow gaps 16G. Four representative rays 18A, 18B, 18C and 18D are illustrated to strike within the spot of illumination 17. Using appropriate optics (e.g., an objective lens on the source 18), the size of the spot 17 may be adjustably selectable to focus on an area containing any arbitrary number of yarns 16Y forming the fabric 16 or down to an area containing only a single filament of a yarn 16Y.

The rays 18A and 18B both define rays of "useful light" in that both rays reflect from the surface 16E of the fabric 16 and pass through the aperture of acceptance 27 for collection by the detector 22. Ray 18A reflects specularly from the surface 16E of the fabric 16 by interaction with one of the filaments of a yarn 16Y comprising the fabric 16. Ray 18B is shown as being capable of entry into and escape from the volume of a filament of a yarn 16Y. As FIG. 3B shows by the nonadjacent entry and exit points of ray 18B in the yarn, a ray could be directed through multiple internal reflections before emerging from a filament toward the aperture of acceptance 27. Although this mechanism may affect the amount of light received by detector 22, rays such as 18B are not believed to significantly affect the invention.

The rays 18C and 18D are rays of "lost" light. The ray 18C in FIG. 3A interacts with one of the filaments 16Y comprising the fabric 16 and reflects in a divergent path away from the axis 24. The ray 18C thus does not pass through the aperture of acceptance 27. As a result, the ray 18C is not collected by the detector 22 and becomes "lost" light. The ray 18D interacts with one of the filaments 16Y of fabric 16 and is not reflected from, but instead, is absorbed into the fabric 16. Such a ray 18D does not enter the aperture of acceptance and is also light "lost" to the detector 22. Light is similarly "lost" when a ray (not shown) undergoes multiple reflections within the yarn and emerges from a filament, but is directed away from the aperture of acceptance 27.

As seen from FIG. 3B, as the fabric stretches, the size of the gaps 16G formed in the monitoring fabric 16 increases. This increase in size of the gaps 16G decreases the likelihood that a photon will usefully reflect toward the detector 22. Thus, the number of rays of useful light (e.g., the ray 18A) decreases from the situation shown in FIG. 3A, while the number of photons lost to the detector 22 by divergence or other mechanisms (e.g., represented by the rays 18B and 18C) increases. The signal output from the detector 22 concomitantly drops. Although the number of photons absorbed (e.g., represented by the ray 18D) does not necessarily change, the amount of yarn 16Y within the spot size 17 decreases, and it becomes less likely that a ray will strike yarn 16Y and be reflected or absorbed.

As the body of the subject S contracts during an exhalation, the fabric 16 undergoes the elastic recovery phase of its stretch. The gaps 16G return to their original size (FIG. 3A). A relatively large portion of the light is again usefully reflected toward the detector 22, increasing the output signal therefrom.

Viewed consecutively these events define a stretch cycle of elongation and recovery. The signal generated at the detector 22 of the monitoring system varies from an initial state to an intermediate state and back to the initial state, as represented by FIG. 3C. This figure graphically illustrates that during the course of a stretch cycle the light balance (reference character "LB" in FIG. 3C) of the fabric changes. Comparison between the initial and inhalation states (indicated by respective reference characters "I" and "II" in FIG. 3C) and between the inhalation and exhalation states (indicated by respective reference characters "II" and back to "I" in FIG. 3C) clearly shows that the amount of light reflected by the monitoring fabric 16 through the aperture of acceptance 27 for collection by the detector changes in a periodic fashion over time as the fabric stretches. Note that light lost to the detector 22 by absorption is neglected. Thus, in FIG. 3C, at the initial state ("I") the useful light represented by the bottom portion below the "LB" is greater than the lost light represented by the upper portion above the "LB". In contrast, at the inhalation state ("II"), the useful light represented by the bottom portion below the "LB" is less than the lost light represented by the upper portion above the "LB".

This periodic variation in light balance is represented by FIG. 3D as a time-varying signal from "I" to "II" to "I" synchronized with the elongation and recovery stages of fabric stretch. This signal is a temporal measure of the underlying physiological processes, which provide the forces causing the elongation and recovery.

Consecutive fabric stretch cycles of elongation followed by recovery provide a periodic variation in light balance synchronized in time (represented in FIG. 3D). Thus, fabric stretch cycles have an associated frequency driven by the frequency of an underlying physiological process. In order to measure the frequency or frequencies of an underlying physiological process(es) or the frequency of any motion driving a fabric stretch cycle, the output from the detector 22 is directed to a data acquisition unit 28. Typically, the data acquisition unit 28 includes a detector signal sampling rate, which is user-selectable in software. For example, if the frequency of normal human respiration rate (15 to 20 per minute) is being measured, an appropriate detector signal sampling rate is selected of less than or equal to 100 Hertz. The sampled signal is optionally filtered with appropriately chosen high and low pass filters to create a cleaner raw signal, performed in software or hardware. The resulting waveform acquired from the data acquisition unit 28 is downloaded to and stored in a suitable computer (e.g., Dell Computer Inc., Mobile Pentium III, 750 MHz CPU). The stored time domain signal is resolvable into a frequency domain spectrum by software methods known to those skilled in the art of using the Fourier frequency deconvolution algorithm. Any frequency greater than that of the chosen lowest frequency expected by the Fourier method appears in the frequency domain spectrum and is thus identifiable, e.g. the rate of respiration sought. Frequencies higher or lower than, for example, typical respiration rates are also resolvable by known variations in the signal processing technique using the Fourier method.

Those skilled in the art will also recognize that the principles underlying the invention as heretofore described can be applied in a variety of other situations where it is desired to monitor the motion of a member. For example, in another embodiment the motion monitoring system of the present invention may be used to monitor movement of a component of a multicomponent structure.

The motion monitoring system for such a usage comprises a textile mantle, at least a portion of which is formed from the monitoring fabric. The term "textile mantle" encompasses any fabric structure covering (in whole or in part) a component of a structure.

The textile mantle is disposed in any convenient manner over the component whose motion is to be monitored. In the same way as heretofore discussed a source 18 and a detector 22 are attached to the textile mantle in relative positions such that the amount of useful light reflected from the fabric 16 through an aperture of acceptance 27 for collection by the detector 22 relative to the amount of light lost to the detector 33 changes as the fabric undergoes a stretch cycle in response to motion of the component.

It may be appreciated from the foregoing that the fabric, garment and system of the present invention provides a particularly useful noninvasive technique for the monitoring of one or more physiological parameters of a subject S without necessitating a change of clothing or the use of a chest or body strap or clamp.

When the fabric is in use, as when incorporated into a garment or mantle, the stretch cycle of elongation and recovery changes, or modulates, the amount of reflected by the monitoring fabric toward the aperture of acceptance.

Those skilled in the art, having the benefit of the teachings of the present invention as hereinabove set forth, may effect modifications thereto. Such modifications are to be construed as lying within the scope of the present invention, as defined by the appended claims.

What is claimed is:

1. A system for monitoring at least one predetermined physiological parameter of a wearer, comprising:

a garment comprising a fabric exhibiting a light reflection property and substantially no light transmission property when the fabric is illuminated with light having wavelength(s) in the range of from about 400 to about 2200 nanometers;

an aperture of acceptance defined with respect to an axis extending from the fabric;

at least one source of radiation having wavelength(s) in the range of from about 400 to about 2200 nanometers to direct radiation onto the fabric;

at least one detector disposed in the aperture of acceptance to detect radiation having wavelength(s) in the range of from about 400 to about 2200 nanometers incident on the detector;

a signal processor for converting a periodically varying signal output from the detector or from a data acquisition unit associated with the detector into a signal representative of a predetermined physiological parameter of the garment wearer; and a conductive pathway disposed on or in the garment connecting the detector and the signal processor;

wherein the source and detector are associated with the fabric in fixed relative positions with respect to the aperture of acceptance such that reception of incident radiation detected by the detector is directly affected by a change in the amount of useful light reflected by the fabric into the aperture of acceptance as the fabric periodically stretches and recovers from stretch in response to at least one predetermined physiological parameter of the garment wearer.

2. The monitoring system of claim 1 wherein the fabric comprises:

a first plurality of reflective yarns knitted or woven with a second plurality of stretchable yarns, wherein each stretchable yarn is formed as a combination of a covered elastic yarn and a hard yarn.

3. The monitoring system of claim 1 wherein the fabric is detachable from the garment.

4. The monitoring system of claim 1 wherein the fabric is integral with the garment.

5. The monitoring system of claim 1 wherein the signal processor is mounted on or in the garment.

6. A system for monitoring motion of a structures comprising:

a textile mantle mounted to at least a portion of the structure, at least a portion of the mantle being formed from a fabric exhibiting a light reflection property and substantially no light transmission property when the fabric is illuminated with light having wavelength(s) in the range of from about 400 to about 2200 nanometers, an aperture of acceptance defined with respect to an axis extending from the fabric;

at least one source of radiation having wavelength(s) in the range from about 400 to about 2200 nanometers;

at least one detector disposed in the aperture of acceptance and responsive to incident radiation having wavelength(s) in the range from about 400 to about 2200 nanometers to produce a signal representative thereof;

a signal processor for converting a periodically varying signal output from the detector or from a data acquisition unit associated with the detector into a signal representative of motion of the portion of the structure; and a conductive pathway disposed on or in the textile mantle connecting the detector and the signal processor;

wherein the source and detector are associated with the fabric in fixed relative positions such that the reception of incident radiation by the detector is directly affected by a change in the amount of useful light reflected by the fabric into the aperture of acceptance as the fabric periodically stretches and recovers from stretch in response to motion of the portion of the structure.

7. The monitoring system of claim 6, wherein the source and detector are attached to the fabric.

8. The monitoring system of claim 6 wherein the fabric comprises:

a first plurality of reflective yarns knitted or woven with a second plurality of stretchable yarns, wherein each stretchable yarn is formed as a combination of a covered elastic yarn and a hard yarn.

9. The system of claim 1 wherein the fabric exhibits the light reflection property when illuminated with light having wavelength(s) in the range from about four hundred (400) nanometers to about eight hundred (800) nanometers;

wherein the source provides radiation having wavelength(s) in the range from about four hundred (400) nanometers to about eight hundred (800) nanometers; and wherein the detector responds to radiation having wavelength(s) in the range from about four hundred (400) nanometers to about eight hundred (800) nanometers.

10. The monitoring system of claim 6 wherein the fabric exhibits light reflection property when illuminated with light having wavelength(s) in the range from about four hundred (400) nanometers to about eight hundred (800) nanometers;

wherein the source provides radiation having wavelength(s) in the range from about four hundred (400) nanometers to about eight hundred (800) nanometers; and wherein the detector responds to radiation having wavelength(s) in the range from about four hundred (400) nanometers to about eight hundred (800) nanometers.

* * * * *

UNITED STATES PATENT AND TRADEMARK OFFICE
CERTIFICATE OF CORRECTION

PATENT NO. : 7,715,897 B2  Page 1 of 1
APPLICATION NO. : 10/937119
DATED : May 11, 2010
INVENTOR(S) : George W. Coulston It is certified that error appears in the above-identified patent and that said Letters Patent is hereby corrected as shown below:

\*\*In Claim 6, in the first line at Column 13, line 25, "structures" should read -- structure, --.

Signed and Sealed this

Twenty-second Day of June, 2010

David J. Kappos
*Director of the United States Patent and Trademark Office*